United States Patent
Barrett et al.

(10) Patent No.: US 8,666,679 B2
(45) Date of Patent: Mar. 4, 2014

(54) MICRO-FABRICATED DOUBLE CONDENSER METHOD AND APPARATUS FOR THE MEASUREMENT OF NUMBER-SIZE DISTRIBUTION OF AIRBORNE NANO-PARTICLES

(75) Inventors: Terence Barrett, Burlington, VT (US); Britt Holmen, Burlington, VT (US)

(73) Assignee: The University of Vermont and State Agriculture College, Burlington, VT (US)

( * ) Notice: Subject to any disclaimer, the term of this patent is extended or adjusted under 35 U.S.C. 154(b) by 504 days.

(21) Appl. No.: 13/077,768

(22) Filed: Mar. 31, 2011

(65) Prior Publication Data

US 2011/0246089 A1    Oct. 6, 2011

Related U.S. Application Data

(60) Provisional application No. 61/319,352, filed on Mar. 31, 2010.

(51) Int. Cl.
*G06F 19/00*    (2011.01)

(52) U.S. Cl.
CPC ..................................... *G06F 19/00* (2013.01)
USPC .......................................................... 702/24

(58) Field of Classification Search
USPC ........................................... 702/24, 182–185
See application file for complete search history.

(56) References Cited

U.S. PATENT DOCUMENTS

2008/0262321 A1 * 10/2008 Erad et al. ..................... 600/301

* cited by examiner

*Primary Examiner* — Edward Raymond

(57) ABSTRACT

A micro-fabricated double condenser method and apparatus for the measurement of number-size distribution of airborne nanoparticles is provided. The invention is an instrument which can measure particle size under 100 nanometers in-situ. The present invention includes features such as a small nanoparticle airborne particulate analyzer, with a voltage-stable and feedback-controlled instrument package. The invention features also include a micro-fabricated nanoparticle charging and sorting device (NCaS). The present invention provides a portable, lightweight, and efficacious particle-sizing instrument that is able to effectively count and size nanoparticles over a wide range of operating conditions.

20 Claims, 14 Drawing Sheets

MICRO-FABRICATED DOUBLE CONDENSER METHOD AND APPARATUS FOR THE MEASUREMENT OF NUMBER-SIZE DISTRIBUTION OF AIRBORNE NANO-PARTICLES

U.S. provisional patent application 61/319,352, entitled "Microfabricated Device For The Measurement Of Number-Size Distribution Of Airborne Nanoparticles", naming Terence Barrett, as inventor, filed 31 Mar. 2010

REFERENCE TO U.S. GOVERNMENT INTEREST

"The U.S. Government has a paid-up license in this invention and the right in limited circumstances to require the patent owner to license others on reasonable terms as provided for by the terms of Grant USDOT DTRT06-G-0018 CFDA 20.701, UTC Core award, awarded by U.S. Department of Transportation."

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith.

BACKGROUND

1. Field of Use

Unregulated nanoparticles are the largest component by number fraction of the particulates in late model vehicle tailpipe exhaust, and are responsible for numerous adverse pulmonary and cardiovascular health effects. Expense, size and weight, and vibrations sensitivity confine the industry standard-instruments able to ascertain the size and number of these fine particulates to lab bench use. To effectively regulate and reduce nanoparticle emissions, inexpensive, small, light, and vibration insensitive nanoparticle analyzing instruments are needed.

This application relates to the measurement of air pollution and in particular to the rapid measurement of the quantity and size distribution of aerosol particles. As vehicle engines become more complex and varied, it becomes necessary to have better systems to determine motor vehicle emissions inventories. To develop accurate ultrafine particle models, the common practice of using engine dynamometers and in-lab testing will need to be replaced with in-situ monitoring of vehicles on the road. However, measurement of engine exhaust particle size is currently done using instruments which are bulky, expensive, and energy inefficient to easily adapt to on-board, in-situ particle measurement.

2. Description of Prior Art

Mobile emission inventories have traditionally been based on average emission performance of small data sets of new car, small-scale used car, or road side measurements. However, these methods are only approximations to the continuously varying emissions of real-world vehicles.

There is a lack of truly portable instruments that can both size and count aerosol particle emissions directly on-board vehicles in real time. For example, starting in 2012, heavy-duty diesel on-board vehicle particle emission monitoring will be required in the United States. One particle emission monitoring system is a partial-flow constant volume sampling system that weighs 120 kg and is available to capture particle emissions via a bag collection system which is available for post particle emission analysis (e.g., particle size and count) in a laboratory.

There are other limitations with current systems for measuring engine exhaust particles, in particular ultrafine particles, or particle sizes less than 100 nanometers. Measuring ultrafine particles is typically done in a laboratory setting. As noted earlier, particulate monitoring instruments are bulky and not designed for in-situ (i.e., on board or real-time) particle monitoring. Those particulate sizing instruments are generally connected to engine dynamometers which are run at loads to roughly simulate on-road conditions and are not suitable for in-situ fleet-wide monitoring of engine exhaust particles.

Additionally, particles are measured by measuring the mass of particles below a certain aerodynamic size collected on a filter. This method has the advantage of simplicity but does not distinguish between large particles, i.e., particles above 100 nm, ultrafine particles (<100 nm), and nanoparticles (<50 nm) which correlate with significant adverse health impacts. Often, the total mass of the smaller particles are often minuscule and indeterminate when compared to that of the larger particles. However, it is the smaller ultrafine and nanoparticles that have a higher mobility into the human lung than the larger particles; and can pass from the lung directly into the bloodstream.

One model of a particle measuring device can measure particle mobility (from which particle diameter is derived) diameters from 0.0025 um to 1.0 um and produce a size vs. count distribution in approximately two minutes. However, the instrument is not ideal for non-laboratory use because it is expensive, requires a high watt source, and takes 2 minutes to make a single size distribution measurement.

In one optical system for measuring particle concentration, light is directed through aerosol particle-laden smoke and the attenuation of the light is measured on a detector to indicate total particle concentration. This method does not measure particle size distribution, however. Another optical method uses light scattering to measure particle size by causing the particles to pass one at a time through a chamber so that scattered light amplitude depends on the particle size. The amplitude is measured by a photomultiplier which produces an electrical signal dependent upon particle size. To isolate single particles for detection, gas sampling must be done at low velocity, and the system is usually provided with very narrow pipes which are subject to contamination, require frequent cleaning, and tend to collect the larger particles before their entry into the sensing chamber. Further, such method of measuring the size of a single particle is very slow, requiring perhaps as much as an hour for a typical measurement.

Electrical methods have the advantage that they can be operated nearly continuously with the results available to the operator after a very short interval of time. In one electrical method described in U.S. Pat. No. 3,114,877 to Dunham, a charging device operates to charge separate groups of aerosol particles passing the device. The particles then flow in a random manner through a field-free region, pass an ion trap and flow to a detector. At the detector, the particles lose their charge and produce a current. Although the detector current in the Dunham apparatus is said to be an index of the number of particles, it is clear that the amplitude of the current is a function of the total charge on all of the particles sensed by the detector at a given moment. Thus, the amplitude of the current is a function of the total surface area of the particles. Because the particles flow in a random manner to the detector, particles having different surface areas (and thus different sizes) lose their charge at the same moment of time to produce the current. Therefore, the output current in the Dunham apparatus is not indicative of the number of particles except when they are of uniform size.

Another method which indicates aerosol particle size distribution is based on the mobility of charged particles in an electric field extending radially across a tube in which the particles flow. Mobility is a measure of the velocity of a charged particle in an electric field, and generally speaking, the higher the charge on the particle the higher the mobility. For a given method of charging a particle, the amount of charge on the particle is a function of the size of the particle. Therefore, mobility is a function of particle size and methods based on particle mobility utilize the difference in mobility to measure particle size distribution. In one such device described in U.S. Pat. No. 3,413,545 to Whitby, clean air is caused to move downwardly in an annular flow path surrounding an elongated electrode extending axially in a cylindrical housing. Charged aerosol particles are introduced around the outer periphery of the flow path of clean air and an electric potential is applied across the elongated electrode and the cylindrical housing. For any given potential, particles having mobility below a certain value will not move radially enough to contact and lose their charge to the elongated electrode before passing its downstream end. An electrometer detects these charged particles which generate a current, the amplitude of which is a function of the total charge on the detected particles. By varying the potential applied to the elongated electrode, more or fewer charged particles will reach the detector and induce the current. By relating the current produced when various potentials are applied to the elongated electrode, a measure of particle size distribution can be obtained. However, a number of factors limit the usefulness of this device for monitoring effluents in stacks of industrial installations, for example. Due to the method of charging, known as diffusion charging, only particles less than about 2 microns diameter can be measured whereas in a typical stack, particles up to 100 microns or more will be present. Further, the diffusion charging method is also inconvenient because it requires a source of compressed air and various thin pipes which are subject to clogging.

Another apparatus for measuring particle size and distribution is described in U.S. Pat. No. 7,098,462 to Chua et al. That micro-fabricated device describes a series of condensers in a fixed electric field, each attached to its own electrometer circuit. The distribution of particle sizes in an aerosol is determined by the fraction collected and measured by each of the condenser/electrometer circuits. However, it will be appreciated that characterizing an aerosol of unknown particle size distribution would require a Chua et al. apparatus having enough condensers and corresponding electrometer circuits for any possible particle size; thus leading to a bulky and inefficient method for measuring particle sizes.

Accordingly, there is a need for a method and apparatus for a compact, low-cost, low power system capable of discriminating and measuring in-situ particle size distribution based on particle mobility in electric fields generated by multiple condensers.

BRIEF SUMMARY

The foregoing and other problems are overcome, and other advantages are realized, in accordance with the presently preferred embodiments of these teachings. The invention provided is a robust and field deployable instrument. The present invention includes features such as a small nanoparticle airborne particulate analyzer, with a voltage-stable and feedback-controlled instrument package. The invention features also include a micro-fabricated nanoparticle charging and sorting device (NCaS). The present invention provides a portable, lightweight, and efficacious particle-sizing instrument that is able to effectively count and size nanoparticles over a wide range of operating conditions.

In accordance with one embodiment of the present invention a portable apparatus for measuring aerosol particle concentration and particle size distribution is provided. The apparatus includes a corona charger for ionizing the aerosol particles; a first condenser for ion trapping aerosol particles charged by the corona charger, and a second condenser connectable to the first condenser, wherein the second condenser is adapted to trap aerosol particles having a plurality of mobilities.

In accordance with another embodiment of the present invention a portable apparatus for measuring aerosol particle concentration and particle size distribution is provided. The apparatus includes a corona charger for ionizing the aerosol particles and a first condenser for ion trapping aerosol particles charged by the corona charger, wherein the first condenser is adapted to trap aerosol particles having a first plurality of mobilities.

The invention is also directed towards a portable apparatus for measuring aerosol particle concentration and particle number size distribution. The apparatus includes a corona charger for ionizing the aerosol particles and a first condenser for ion trapping aerosol particles charged by the corona charger, wherein the first condenser is adapted to trap aerosol particles having a first mobility. Also included is a second condenser connectable to the first condenser, wherein the second condenser is adapted by an adjustable power supply to trap aerosol particles having a plurality of mobilities. Included is a measurement board for determining particle sizes and number concentrations in the aerosol; and a control board for: monitoring measurements by the measurement board, adjusting the pump controller, adjusting the first adjustable high voltage power supply, adjusting the second adjustable high voltage power supply, and adjusting the third adjustable high voltage power supply.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Figure 1:
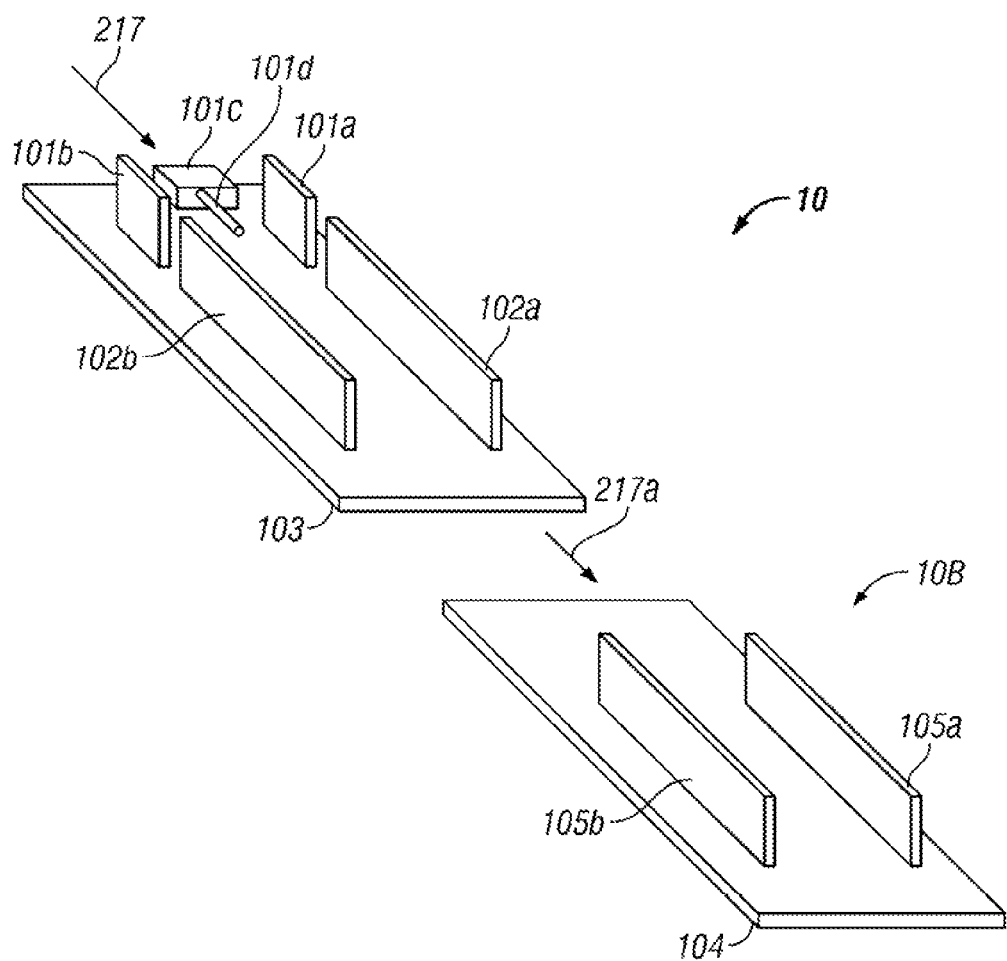
FIG. 1 is pictorial illustration of one embodiment of the miniaturized micro-fabricated double condenser in accordance with the present invention.
Figure 5A:
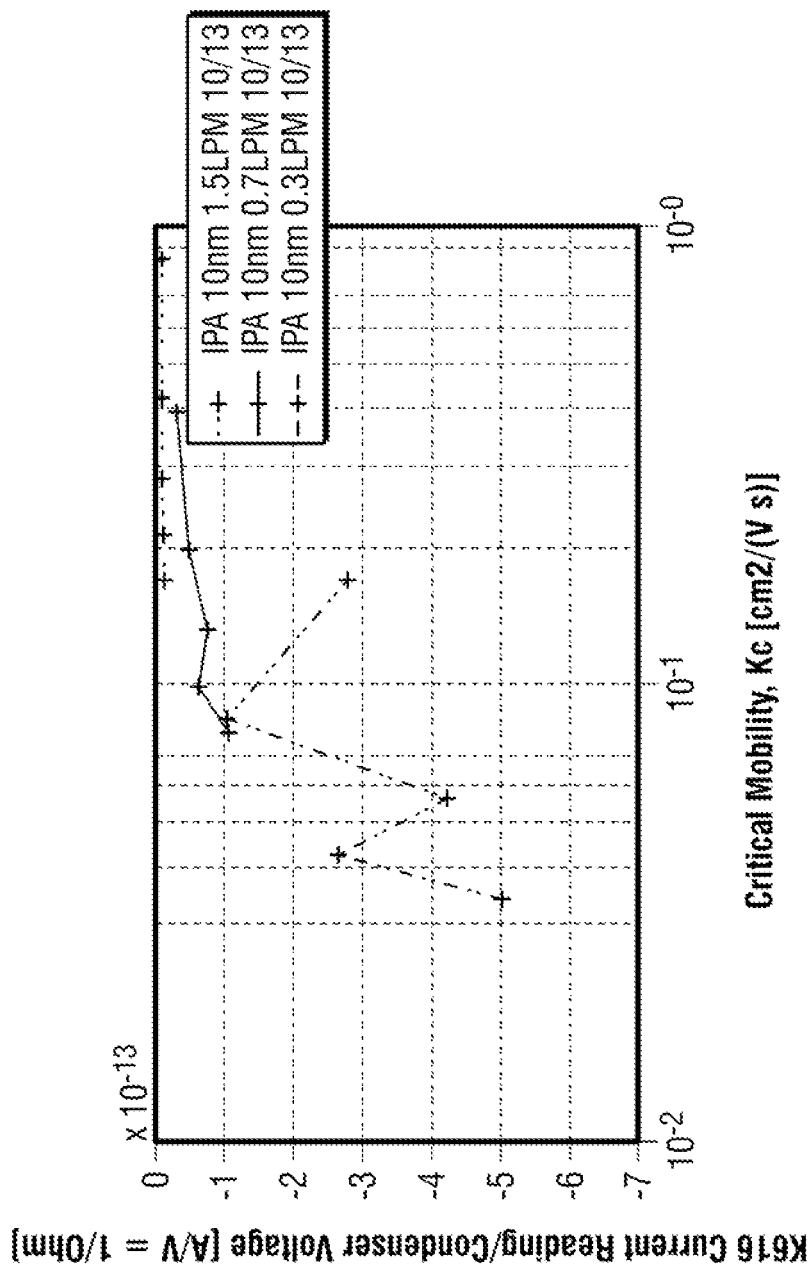
FIG. 5A is a graphical depiction of current reading/condenser voltage versus critical mobilities for multiple concentrations of isopropanol (IPA) in accordance with the present invention shown in FIG. 2.
Figure 5B:
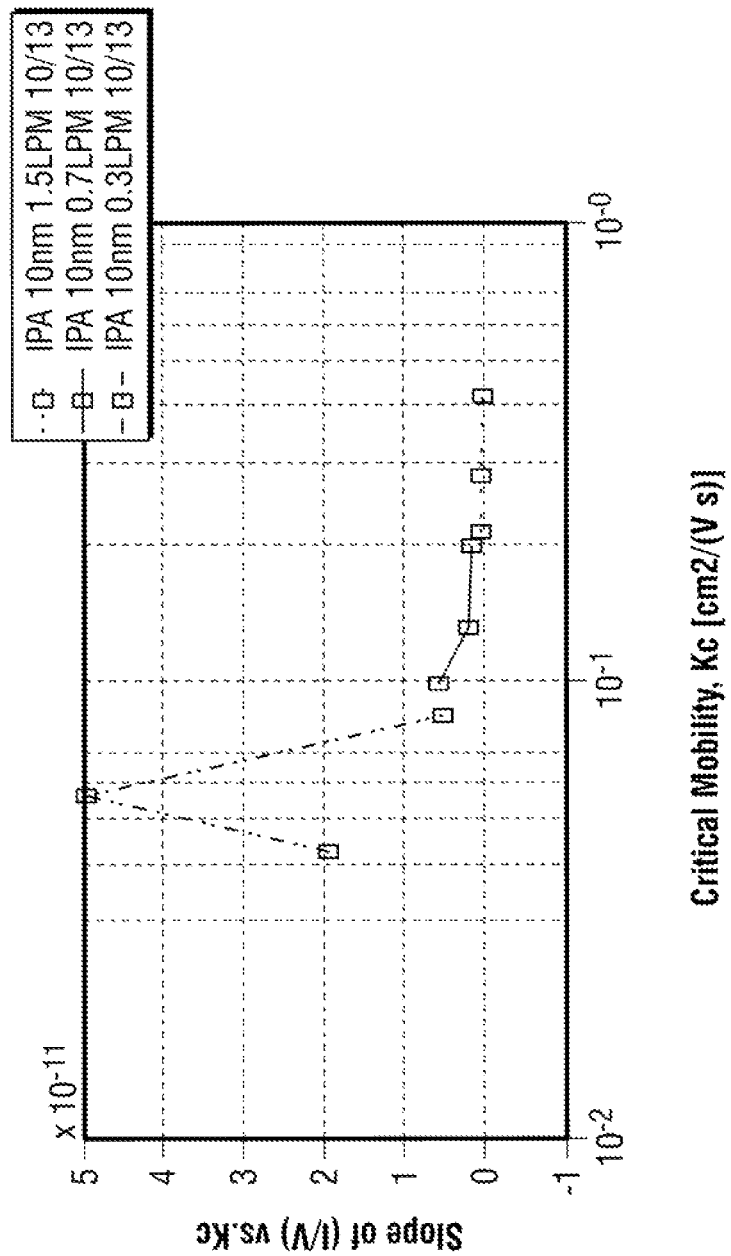
FIG. 5B is a graphical depiction of slopes of current/voltage versus critical IPA mobilities in accordance with FIG. 5A.
Figure 5C:
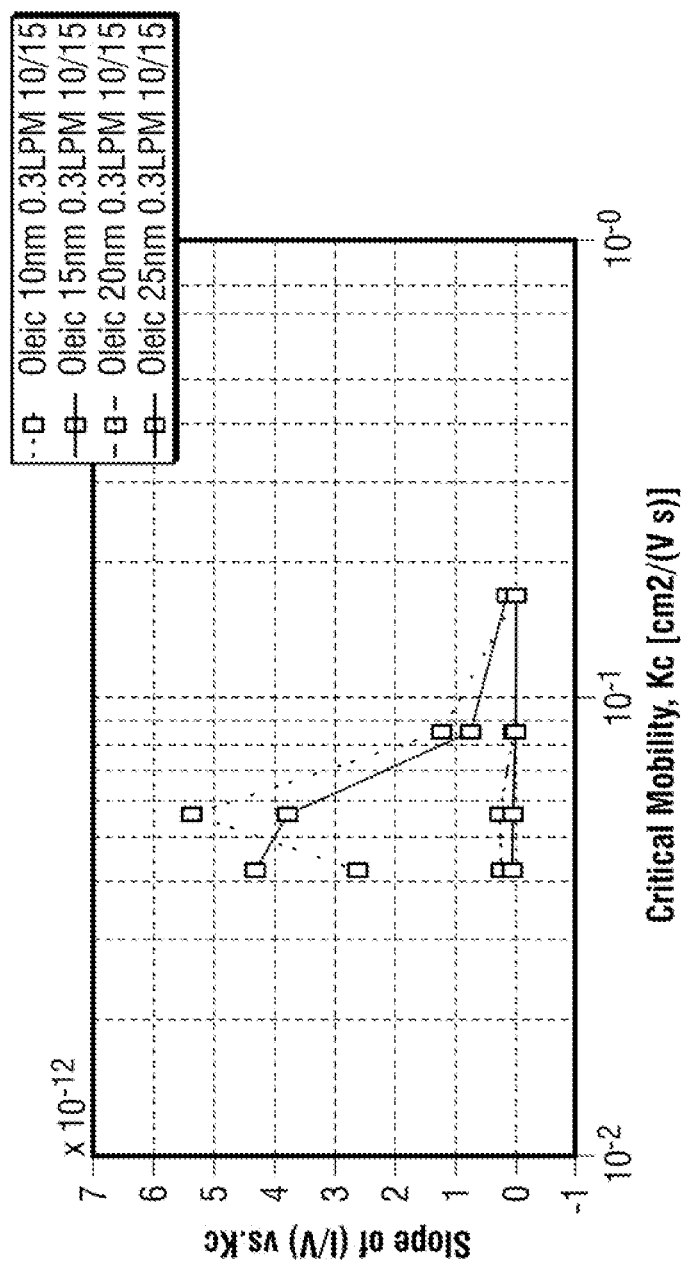
FIG. 5C is a graphical depiction of current reading/condenser voltage versus critical mobilities for multiple oleic acid particle diameters in accordance with the present invention shown in FIG. 2.
Figure 5D:
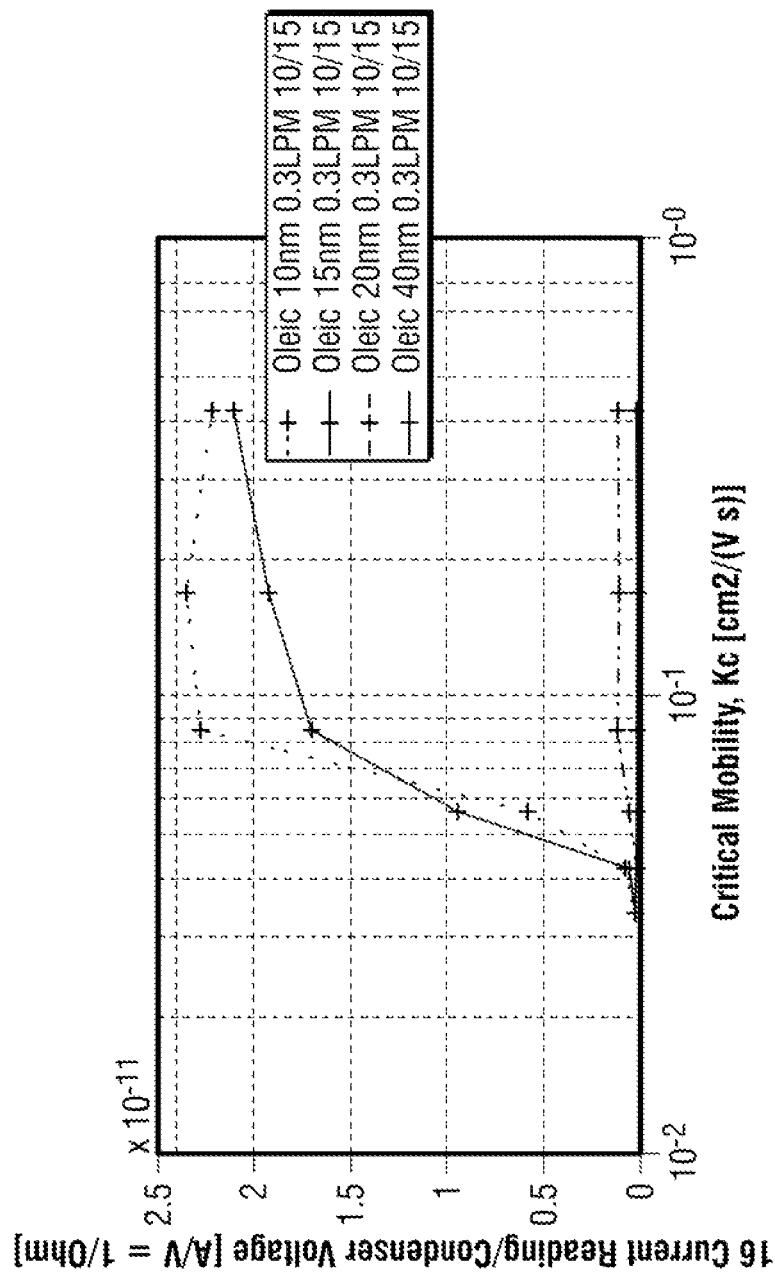
FIG. 5D is a graphical depiction of slopes of current/voltage versus critical oleic acid particle mobilities in accordance with FIG. 5C.
Figure 6A:
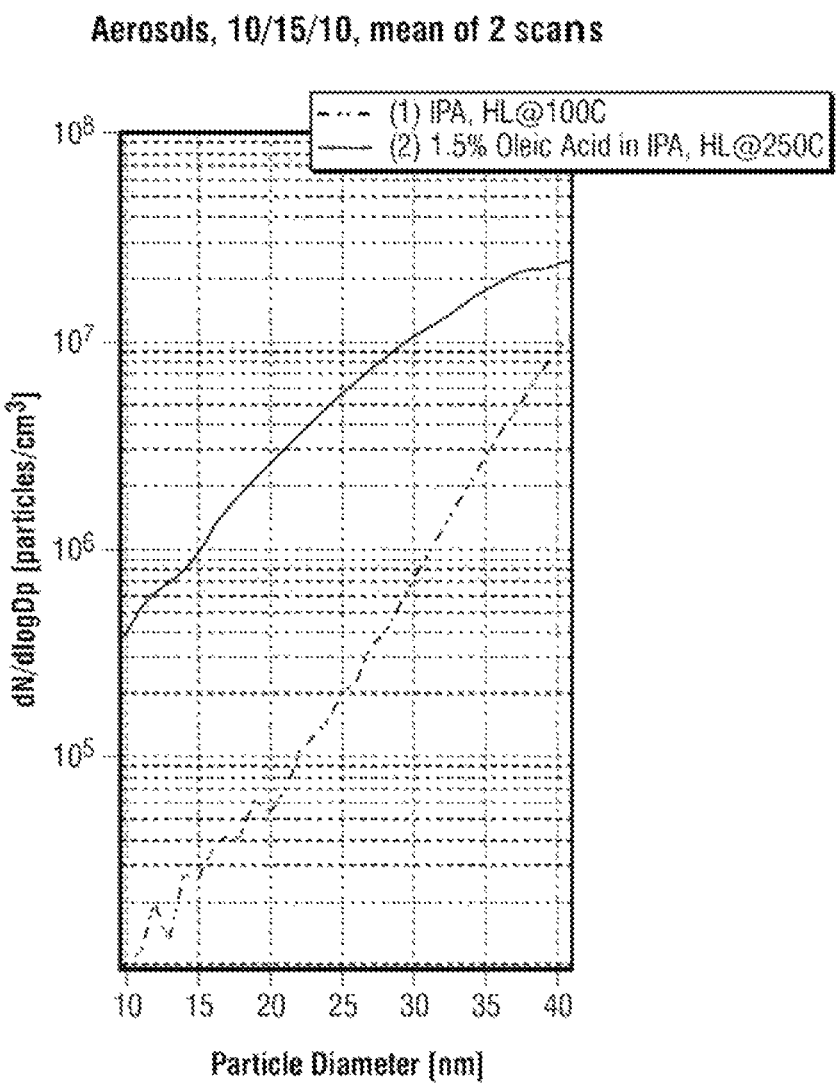
FIG. 6A is a graphical depiction of a number distribution of IPA and oleic acid particles in IPA versus particle diameter in accordance with the present invention shown in FIG. 2.
Figure 6B:
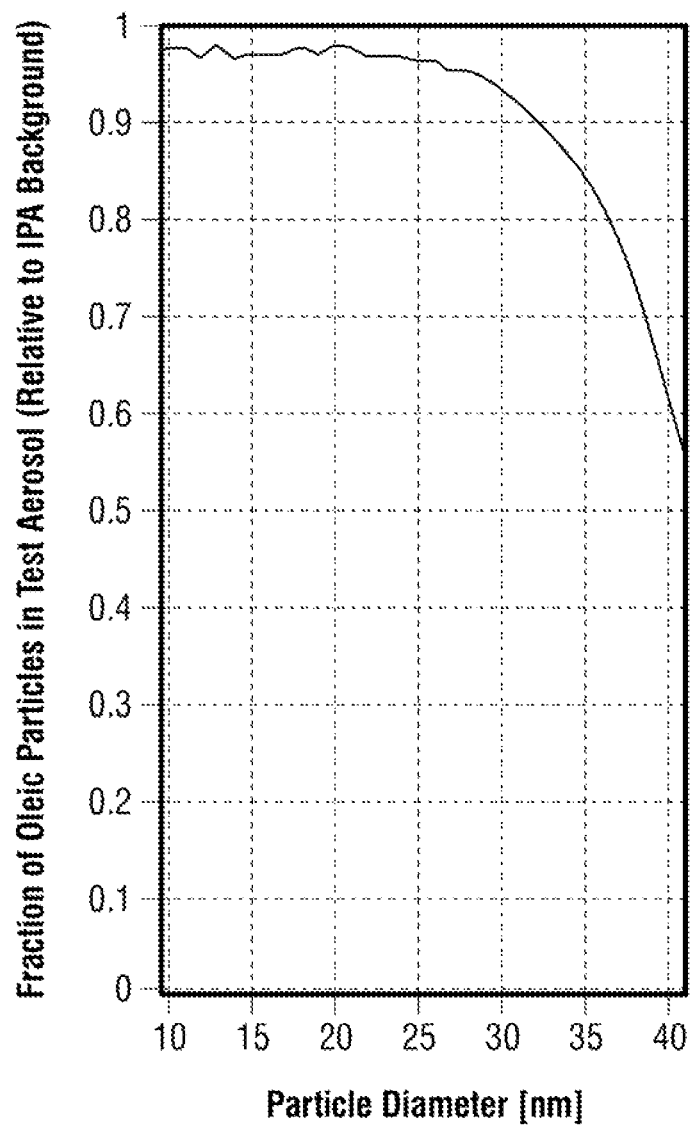
FIG. 6B is a graphical depiction of a fraction of oleic acid particles in IPA versus particle diameter in accordance with the invention shown in FIG. 2.

Referring to FIG. 1 there is shown a pictorial illustration of one embodiment of the miniaturized micro-fabricated double condenser in accordance with the present invention. This embodiment includes a charger 101D and two aspiration capacitors in series 102a, 102b and 105a, 105b. Both aspiration capacitors would nominally be held at the same voltage, but optionally may use separate high voltage power supplies to reduce the likelihood that the current signals to the respective electrometers would be confounded; only one differentiation of the I/V curve of the second condenser 10B would give the number of particles in a given size bin. (See FIG. 5A.)

The first condenser 102a, 102b serves two critical functions: it acts like the sheath air, separating the response of the different particle sizes so they are not confounded, and it serves as an ion trap, reducing the prevalence of combined charging. With this design, the I/V vs. mobility (k) characteristic is the same for a given set of design parameters, and so various settings of potential (V) and flow rate (Q) can be selected that will maximize the possible range of sampled critical mobilities; discussed in more detail herein.

The size distribution is determined from the I/V vs. k characteristic as shown by Eq. 8. (See paragraph 49.) Differentiating Eq. 8 with respect to critical mobility $k_c$ results in Eq. 9. (See paragraph 49.) Plotting $I_3/V_3$ vs. $k_c$ for all settings of $V_3$ and $Q_a$, results in a curve where the slope of the curve at each selected value of $k_c$ provides the number of particles in the mobility range $k_d$ to $k_c$. See FIGS. 5A-5D and FIGS. 6A-6B.

The series embodiment of the present invention supports a sweep V and/or Q operation. This embodiment supports the linear sweep of voltage and/or flow rate, and is able to measure a continuously varying I/V response. This embodiment could be extended in this way to give a direct (non-differentiated) measurement of the particle size distribution. The linear sweeping of V and Q will obviate the need to differentiate the resulting IN curve.

There are four parameters of interest to the characterization of charging efficiency: intrinsic charging efficiency ($\epsilon_i$), the fraction of originally neutral particles which become charged within the charger; extrinsic charging efficiency ($\epsilon_e$), the fraction of originally neutral particles which emerge out of the charger carrying at least one unit of charge; diffusion loss (LD), the fraction of particles lost in the charger through diffusion to the walls; and electrostatic loss (LE), the fraction of particles lost in the charger through electrical attraction to the plates that create the corona-inducing field. The four parameters are represented as:

$$\epsilon_i = (C_1 - C_3)/C_1 \qquad \text{EQ. 1}$$

$$\epsilon_e = (C_2 - C_3)/C_O \qquad \text{EQ. 2}$$

$$LE = \epsilon_i - \epsilon_e \qquad \text{EQ. 3}$$

$$LD = (1 - \epsilon_i)(1 - C_1/C_O) \qquad \text{EQ. 4}$$

Four measurements are undertaken for each corona voltage ($V_1$), flow rate ($Q_a$), and particle size (Dp) combination to be characterized in order to calculate the above four parameters: First, the CPC measured concentration ($C_O$) when the charger and an electrostatic precipitator (ESP) are bypassed; second, the CPC measured concentration ($C_1$) when the voltages of both charger and ESP are zero; third, the CPC measured concentration ($C_2$) when the charger is at its set point voltage and the ESP is set at voltage ($V_{IR}$) sufficient to remove the free ions only; and fourth, the CPC measured concentration ($C_3$) when the charger is at its set point voltage and the ESP is set a voltage ($V_{PR}$) sufficient to remove all charged particles.

Figure 2:
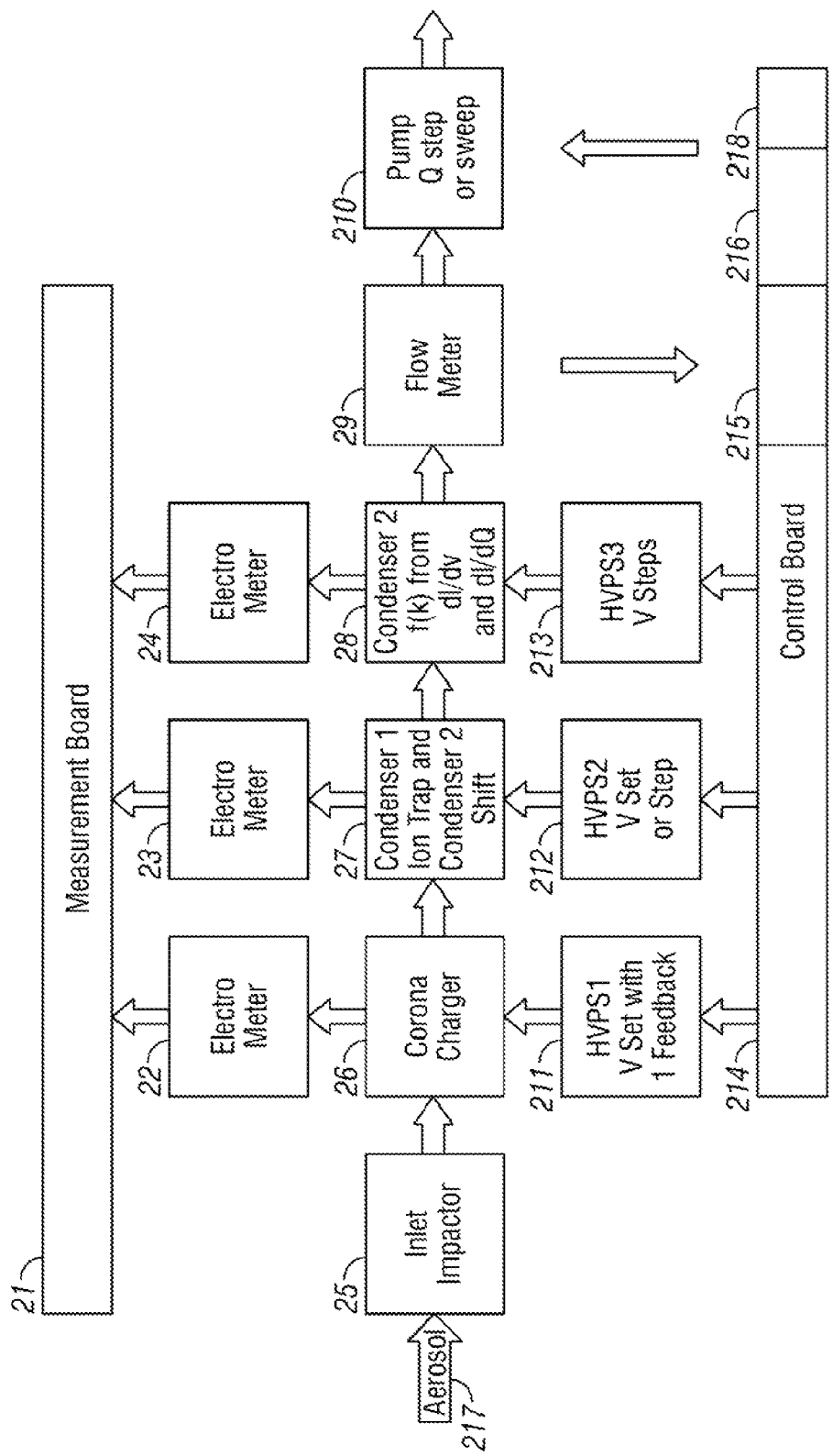
FIG. 2 is an operational control system diagram for the measurement of number-size distribution of airborne nanometer-particles in accordance with the present invention shown in FIG. 1.

Testing the present embodiment of the miniaturized micro-fabricated double condenser 10 shown in FIG. 2 includes a radioactive neutralizer in order to re-neutralize the charged mono-disperse aerosol provided by a Differential Mobility Analyzer (DMA). First, an optimum corona voltage ($V_1$) can be selected. Then, over the range of condenser voltages ($V_2=V_3=V$) and aerosol flow rates ($Q_a$) for each particle diameter (Dp), the curve of $I_3/V_3$ vs. $k_c$ will be recorded, and then numerically differentiated once to determine the number of particles in a given size bin (as described earlier), where the bin extent is defined by the mobility range $k_d$ to $k_c$, with the capacitances determined by the direct measurement method and the relative measurement method. The bins can be adjusted until each mono-disperse aerosol is detected by a single bin. This will provide the relationship between $D_p$ and $k_c$ that will be used for calculating the size distribution of a poly-disperse aerosol.

Figure 7:
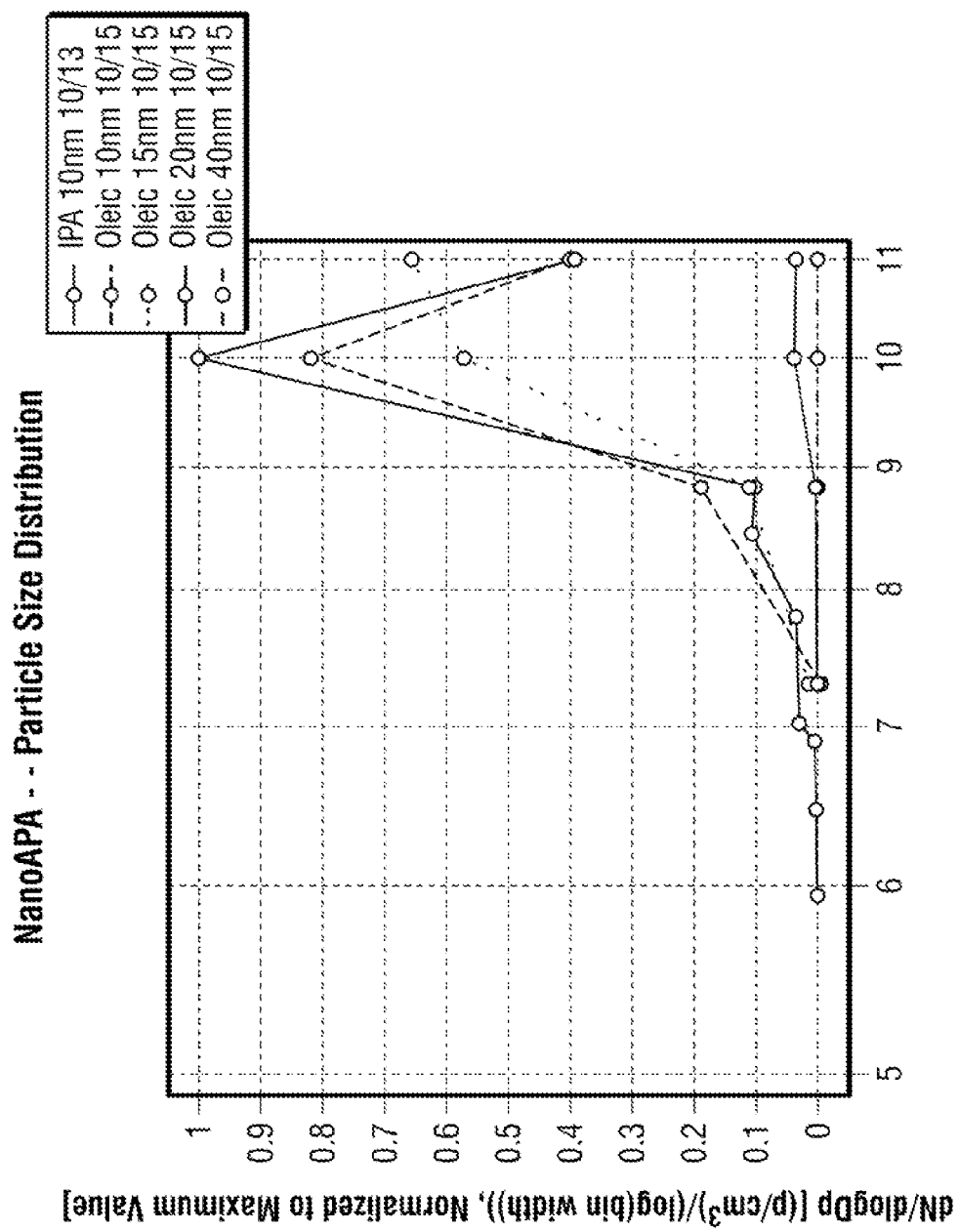
FIG. 7 is a graphical depiction of size distribution measurements for IPA and oleic acid aerosols.

It will be appreciated that the present invention also enables a size distribution measurement of a poly-disperse aerosol. (See FIG. 7). The size distribution measurement is made by measuring the mobility distribution of a poly-disperse aerosol; assigning a $D_p$ to each mobility bin; correcting the counts in each bin using the charger extrinsic efficiency for each bin's $Q_a$ and $D_p$; and correcting the counts in each bin with the charge distribution (which will shift the multiply-charged fraction of a bin to larger $D_p$ bins). The system may be further extended with a single new NCaS device that implements the series/parallel design for direct measurement of the size distribution or a NCaS device and electronic circuit suitable to implement the V and/or Q sweep method.

DETAILED DISCUSSION

Referring still to FIG. 1 there is shown pictorial illustration of one embodiment of the miniaturized micro-fabricated double condenser 10 in accordance with the present invention. The components of the micro-fabricated corona ionizer are deposited on an insulating substrate 103. One possible material for insulating substrate 103 is glass; although it will be appreciated that any suitable insulating substrate may be used. Anchor 101 is deposited on substrate 103. A typical material for anchor 101 is copper; although it will be appreciated that any suitable anchoring material may be used. Grids 101a, 101b are suitably deposited and anchored on the substrate 103 such that they are parallel to probe 101d and equidistant from probe 101d. In this configuration, the corona ionizer forms a flow-through ionizer, which is useful for creating micro-fabricated particulate sensors.

Probe 101d is deposited with anchor 101c but is undercut so that it is suspended above substrate 103. The radius of the tip of probe 101d is typically less than approximately 20 μm, while the suspension height of probe 101d above substrate 103 is typically less than 500 μm.

Still referring to FIG. 1, differential mobility separator plates 102a and 102b are deposited on the substrate 103 such that airflow passing the ionizer is directed between mobility separator plates 102a and 102b. When a potential difference is applied between mobility separator 102a and 102b, an electric field is created between them.

Figure 3:
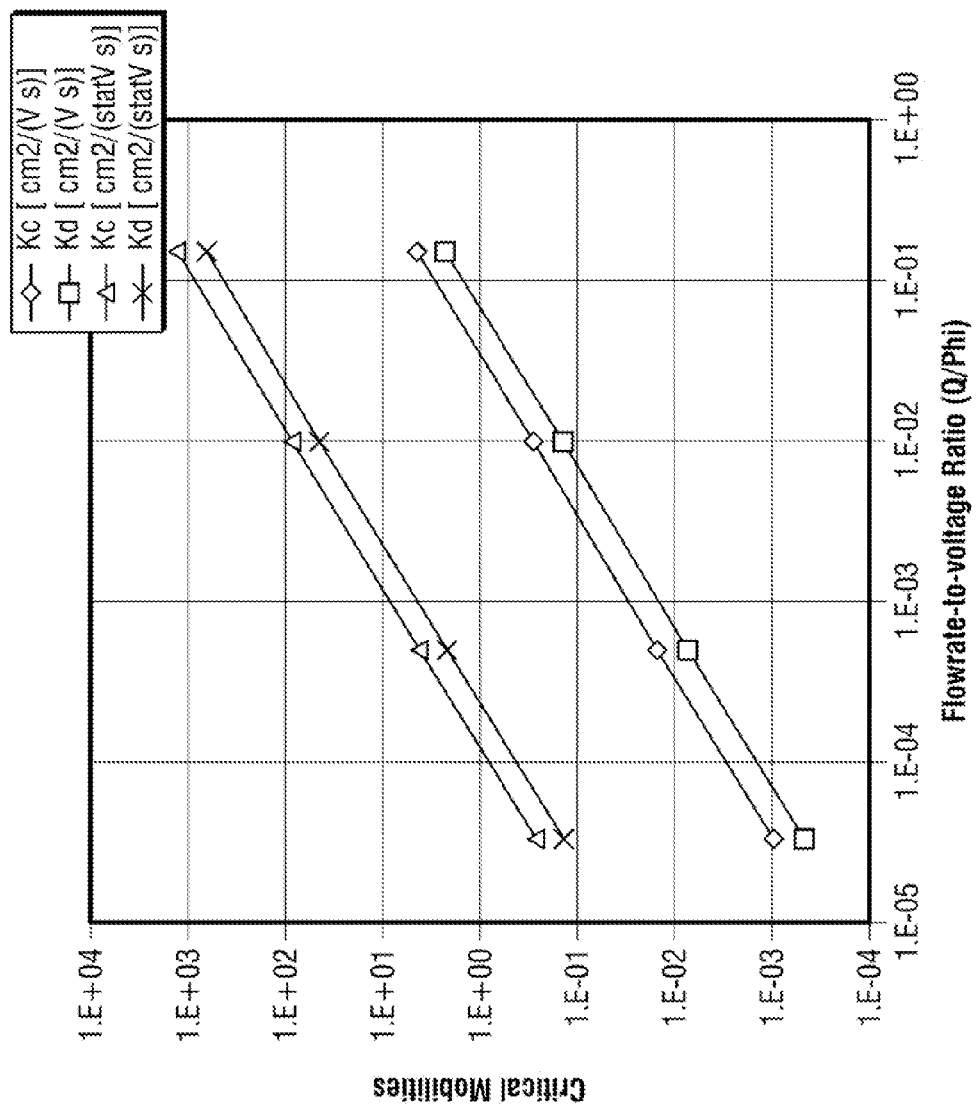
FIG. 3 is a graphical depiction of calculations verifying scalability of design to nanometer dimensions and operating parameter ranges in accordance with the present invention shown in FIG. 1, where critical mobilities on the y-axis are plotted as a function of flow rate (l/min)-Voltage (V) ratio on the x-axis (shown in FIG. 3 as (Q/Phi))
Figure 4A:
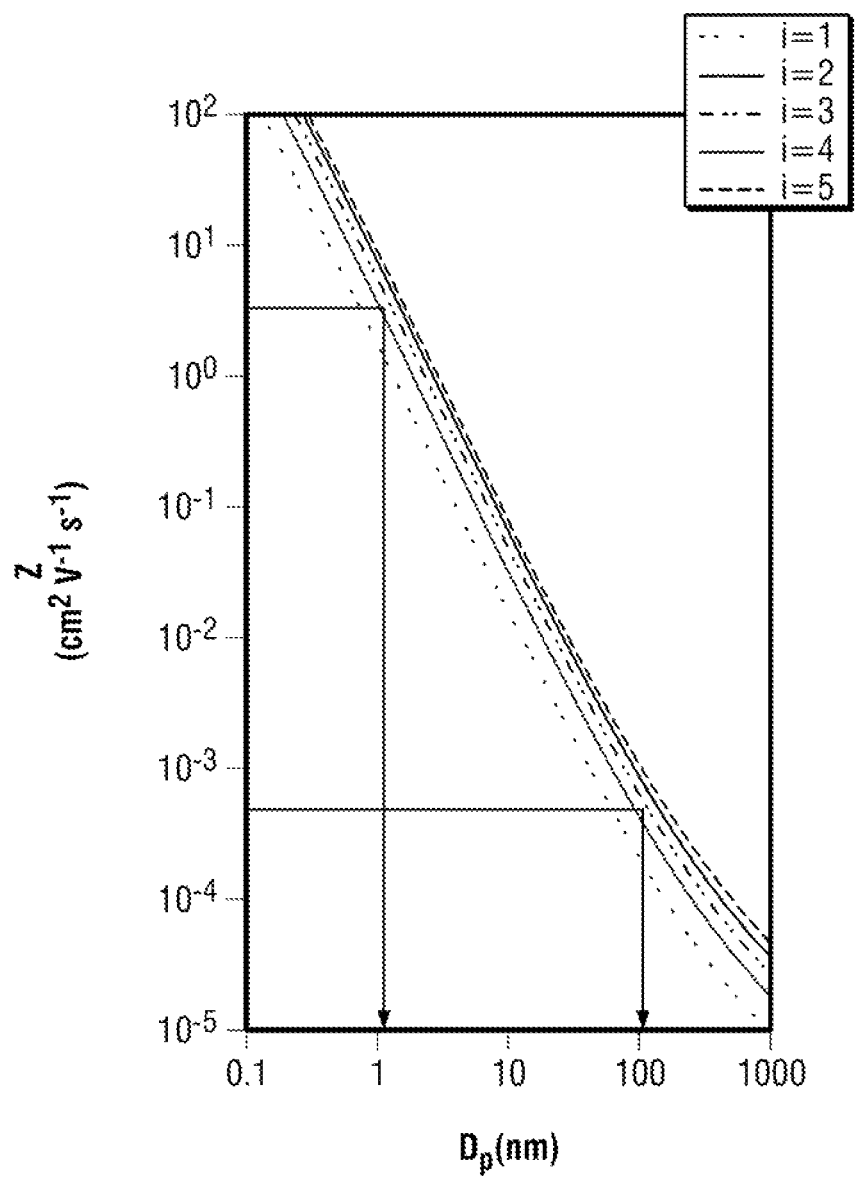
FIG. 4A is a graphical depiction of electrical mobility versus particle diameter in accordance with the present invention shown in FIG. 2.
Figure 4B:
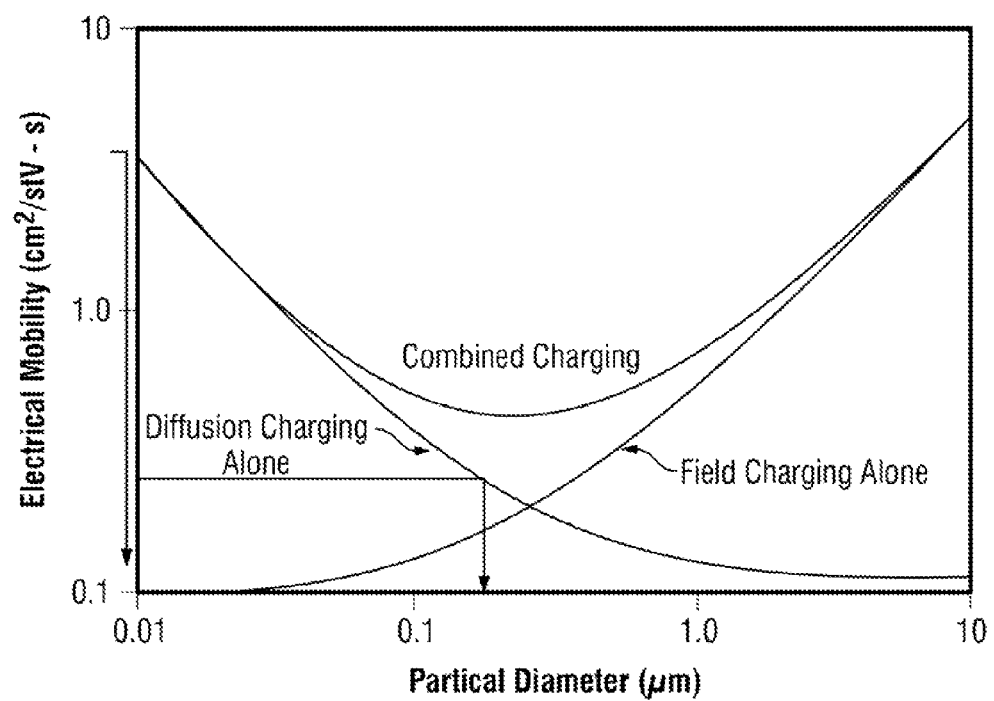
FIG. 4B is a graphical depiction of types of particle charging as a function of electrical mobility and particle diameter in accordance with the present invention shown in FIG. 2.

When charged particulates enter the space between mobility separator plates 102a and 102b, they are deflected by the electric field. The amount of deflection is dependent upon the mobility of the particulates and the strength of the applied field. By varying the voltage applied to mobility separator plates 102a and 102b, particulates of different mobility can be made to impinge on mobility separator plates 102a and 102b and the resultant current can be measured as discussed herein to determine the concentration of particulates with a given mobility. It will be understood that a relationship can be established between a particle's mobility and its diameter. (See FIG. 4A and FIG. 4B.) With general regard to aerosol technology and particle measurement, reference can be had to Flagan, R. C. (1998). "History of electrical aerosol measurements." Aerosol science and technology 28(4)"; and, Hinds, W. C. (1999). "Aerosol Technology: Properties, Behavior, and Measurement of Airborne Particles." New York, John Wiley & Sons. See also FIG. 3, where there is shown a graphical depiction of calculations verifying scalability of design to nanometer dimensions and operating parameter ranges in accordance with the present invention shown in FIG. 1.

Charged particles not collected by mobility separator plates 102a and 102b flow into the second series connectable condenser 10B. Condenser 10B includes mobility separator plates 105a and 105b deposited on substrate 104. Mobility separator plates 105a and 105b are suitably charged to collect charged particles of interest.

Referring also to FIG. 2 there is shown an operational control method diagram for the measurement of number-size distribution of airborne nanometer-particles in accordance with the present invention shown in FIG. 1. The control board 214 applies a control voltage to the high voltage power supply (HVPS) 211 driving a high voltage output ($V_1$) to the micro-fabricated corona charger 26. A corona develops on the end of the probe pin 101a, and electrons from the corona, propelled by the electrical field, drift between the condenser plates 102a, 102b. This establishes a leakage current between pin 101d and plates 101a, 101b which is amplified by a corona electrometer 22 and recorded by measurement board 21. The average number of charges acquired by each particle can be determined based on a function of charger voltage, aerosol flow rate, and particle diameter.

Still referring to FIG. 2, pump 210 is adjusted to pull aerosol at a desired flow rate (Q) thru the miniaturized micro-fabricated double condenser 10. Flow rate is monitored by flow meter 29.

Still referring to FIG. 2, HVPSs 212, 213 provide high voltage outputs ($V_2$ $V_3$) establishing electric fields in condenser 27 and condenser 28, respectively.

The inertial impactor 25, filters the aerosol 217 to pass particle diameters of interest to the corona charger 26. It will be appreciated that any suitable method for filtering particles of interest may be used.

The aerosol then passes thru the corona charger 26 and its particles are ionized.

The charged particles of the aerosol then flow into the first condenser 27 and begin to flow toward the condenser plate 102*a* or 102*b* with the opposite charge. Charged particles with an electrical mobility greater than the critical mobility of the condenser for this flow rate and voltage are collected on the condenser plate 102*a* or 102*b*. (This includes the air molecules ionized by the corona.) The critical mobility of the first condenser is:

$$k_c=Q_a/(4\pi C_1 V_2) \quad \text{Eq. 5}$$

where:

C, is the capacitance of the condenser, estimated by:

$$C_1=A/4\pi d \quad \text{Eq. 6}$$

where:

A is the condenser plate area; and d is the condenser plate separation.

When the charged particles stick to the condenser plate 102*a* or 102*b*, the particle transfers it charge, which become a current that is amplified by the electrometer 23 and recorded by measurement board 21.

Charged particles not collected by the first condenser flow into the second condenser 28 where they are driven to the opposite charged plate of this condenser as described earlier. Charged particles with a critical mobility greater than the critical mobility $k_d$ of both condensers combined but less than $k_c$, because the particles were not collected in the first condenser 27, are collected in the second condenser 28. The critical mobility $k_d$ of both condensers combined is described as:

$$k_d=Q_a/(4\pi(C_1+C_2)V_3) \quad \text{Eq. 7}$$

It will be understood that there is also a fraction of charged particles with mobilities less than $k_d$ that gets collected; this can be taken into account, as shown in the data analysis below.

The current from these collected charges is amplified by electrometer 24 and recorded by measurement board 21. The aerosol with whatever particles still remain in it passes that the flow meter and pump and exits the instrument.

This process is repeated over a range of airflow $Q_a$ and voltage ($V_2$,$V_3$) values, with the current from the second condenser 28 recorded at each setting. The airflow and voltage values are selected to provide values of the critical mobilities that will define particle diameter ranges that are of interest.

The recorded data is arranged as $I_3/V_3$ vs. $k_c$ and differentiated once in accordance with Eq. 9. This information, along with Eq. 8 below, and the corrections calculated from the instrument characterization (described above) results in the number vs. diameter distribution, f(k), of the aerosol sample, the desired measurement.

$$I_3/V_3 = 4\pi e [C_1 k_d \int_{k_d}^{k_c} f(k)dk + (C_1+C_2) \int_0^{k_d} kf(k)dk - C_1 \int_0^{k_c} kf(k)dk] \quad \text{Eq. 8}$$

Where:
$I_3$=second separator current
$V_3$=second separator voltage
$C_1$=Condenser 1 capacitance
$C_2$=Condenser 2 capacitance
e=electron charge
$k_c$=first condenser critical mobility
$k_d$=second condenser critical mobility
f(k)=mobility spectrum of the sample aerosol $$\frac{d\left(\frac{I_3}{V_3}\right)}{dk_c} = \frac{\partial\left(\frac{I_3}{V_3}\right)}{\partial k_c} + \frac{\partial\left(\frac{I_3}{V_3}\right)}{\partial k_d}\frac{dk_d}{dk_c} = 4\pi e C_1 \int_{k_d}^{k_c} f(k)dk \quad \text{Eq. 9}$$

Still referring to FIG. 2, control board 214 may be any suitable computer/microcontroller. For example, computer/microcontroller 214 and measurement board 21 may be, or include, a "mote" 215. As used in this disclosure, the term "mote device" or "mote" typically indicates an autonomous or semi-autonomous computing; communication, actuating, and/or sensing device as described in the mote literature (e.g., Intel Corporation's, or Crossbow Inc.'s mote literature).

Certain embodiments of the mote device(s) 215 can be fabricated to be relatively small (typically less than several inches in dimension, often a fraction of an inch). Certain embodiments of mote systems(s) can be relatively inexpensive to produce, and can be designed to stand up to relatively harsh and/or external environments.

Many embodiments of mote systems(s) 215, or simply "motes", as described in this disclosure can provide a wide variety of parameter sensing and/or actuating functionalities. Such parameter sensing may be controlled (and/or light or display device actuated) using computer-based sensing, electro-mechanical sensing, magnetic sensing, and/or other sensing techniques. Certain embodiments of mote device(s) and networks can be located at remote, hostile, external, or inaccessible location(s); and can be wirelessly networked.

Still referring to FIG. 2, control board 214 may also include a Global Positioning Satellite (GPS) transceiver 216 for determining location information associated with particle measurements. In addition, control board 214 may also include a radio frequency identification tag (RFID) 218, passive, active, or a hybrid. RFID tags are well known in the art and need not be discussed here.

It will be appreciated that the invention described herein advantageously provides particle diameter measurement and particle count for a range of nanoparticle diameters over a range of operating conditions suitable for on-board exhaust sampling of spark and compression ignition vehicles and for road-side exhaust sampling in a miniaturized package. The effect of the first condenser is to simplify the data inversion and to improve the signal-to-noise ratio. And, as described above, the two condensers working in tandem sweep through a range of voltage settings, and the particles collected by the second condenser are measured by a single electrometer.

It will be further appreciated that the miniaturized voltage-stable, and feedback-controlled instrument package includes a novel, micro-fabricated nanoparticle charging and sorting device (NCaS) (see FIG. 1). Using the separator portion of the NCaS device as an aspiration capacitor, also known as an ion condenser) advantageously removes, the requirement for a separate particle separation step using a Faraday cup; this further reduces the size and weight of the device.

Another advantage of the present invention is that the parallel condenser plates 102a, 102b and 105a, 105b, are held at a potential voltage difference and the current through that circuit is monitored as the charged particles of the sample aerosol are collected on one of the condenser plates and release their electrons.

Alternate Invention Embodiment Discussion

Figure 8:
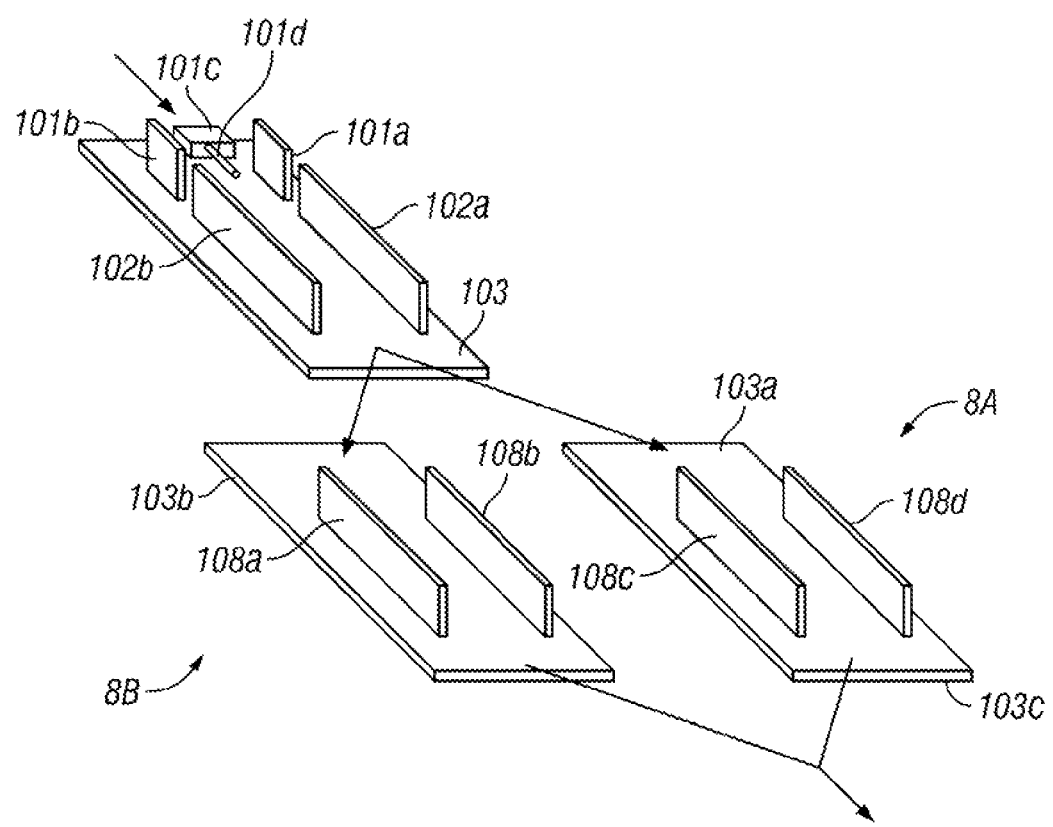
FIG. 8 is a pictorial illustration of an alternate charger+series/parallel aspiration capacitor embodiment of the present invention shown in FIG. 1.

Referring also to FIG. 8 there is shown a pictorial illustration of an alternate charger+series/parallel aspiration capacitor embodiment of the present invention shown in FIG. 1. This embodiment requires at least three NCaS devices, or one enhanced NCaS device integrating the function of at least three of the NCaS devices. This embodiment allows for the direct (non-differentiated) measurement of the particle size distribution. In essence, the parallel capacitors 8A, 8B (held at slightly different voltages) do the work of the double differentiation.

Still referring to FIG. 8, differential mobility separator plates 102a and 102b are deposited on the substrate 103 such that airflow passing the ionizer is directed between mobility separator plates 102a and 102b. When a potential difference is applied between mobility separator 102a and 102b, an electric field is created between them.

When charged particulates enter the space between mobility separator plates 102a and 102b, they are deflected by the electric field. The amount of deflection is dependent upon the mobility of the particulates and the strength of the applied field. By varying the voltage applied to mobility separator plates 102a and 102b, particulates of different mobility can be made by control board (FIG. 2-214) to impinge on mobility separator plates 102a and 102b and the resultant current can be measured by measurement board (FIG. 2-21) as discussed herein to determine the concentration of particulates with a given mobility. It will be understood that a relationship can be established between a particle's mobility and its diameter. Charged particles not collected by mobility separator plates 102a and 102b flow into condensers 8A and 8B. Condenser 8A includes mobility separator plates 108c and 108d deposited on substrate 103c. Mobility separator plates 108c and 108d are suitably charged to collect charged particles of interest.

Similarly, condenser 8B includes mobility separator plates 108a and 108b deposited on substrate 103b. Mobility separator plates 108a and 108b are suitably charged to collect charged particles of interest.

Figure 9:
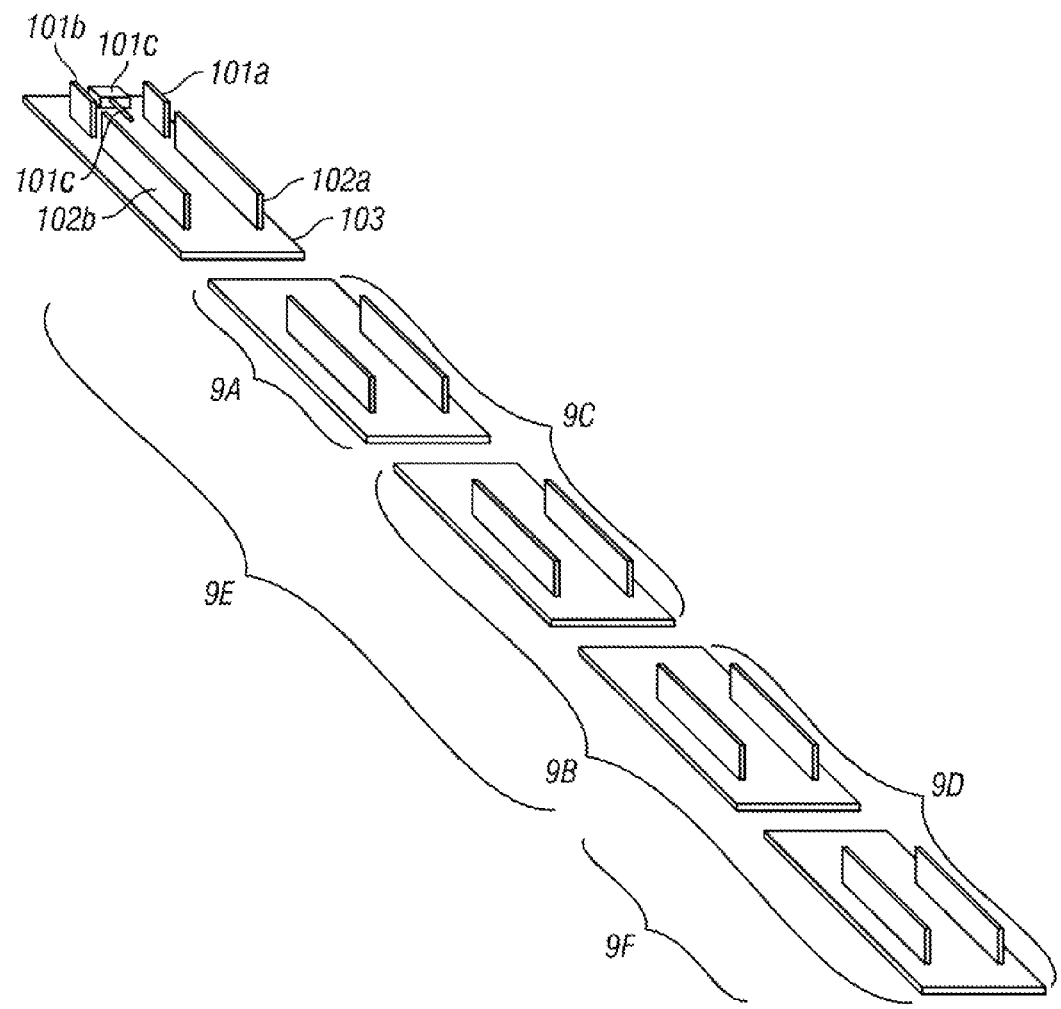
FIG. 9 is a pictorial illustration of an alternate switchable series condenser configuration of the present invention shown in FIG. 1.

Referring also to FIG. 9, there is a pictorial illustration of an alternate switchable series condenser configuration of the present invention shown in FIG. 1. Switching the segmented condenser sections via control board (FIG. 2-214) into varying lengths, for example 9E and 9F, allows the overall ratio of critical mobilities to be varied, providing for a user-selectable accuracy/precision tradeoff.

Still referring to FIG. 9, condenser stages 9C and 9D can be switched off or on in the high voltage and electrometer circuits (See FIG. 2), so that the critical mobility of the two stages 9C, 9D can be equally raised or lowered. Also, using one condenser in each stage and then the other would extend the time between cleaning or condenser replacement.

It should be understood that the foregoing description is only illustrative of the invention. Thus, various alternatives and modifications can be devised by those skilled in the art without departing from the invention. Accordingly, the present invention is intended to embrace all such alternatives, modifications and variances that fall within the scope of the appended claims.

For example, referring again to FIG. 1, it will be understood that in the event of a malfunction of the second condenser 10B, the invention can operate in Charger+single Aspiration Capacitor mode. This mode uses a single NCaS device plus an electrometer circuit to measure the current induced by the charges collected to the separator plates 102a and 102b. This mode requires a double differentiation, but now of the I/V curve. Operationally this is accomplished as two single differentiations for the tangent intercepts to determine the number of particles in a single size bin.

In addition, the present invention and embodiments are constricted with suitable materials to withstand and operate in a temperature range of approx. −20 to 300 C (from the ambient temperatures in the winter of northern climates to tailpipe exhaust temperatures); relative humidity from zero to fully saturated (encountered in both the ambient air and in direct vehicle exhaust); particle compositions both hydrophobic and hydrophilic; particle morphologies both simple and agglomerated (to cover both the nucleation and the accumulation modes of the particle spectrum, the latter especially an issue with diesel exhaust, which forms long-chain agglomerates); a particle diameter range of 10-300 nm to cover the high end of the nucleation mode and the low end of the accumulation mode; and a size-bin resolution sufficient to clearly differentiate the two modes.

What is claimed is:

1. A portable apparatus for measuring aerosol particle concentration and particle size distribution, the apparatus comprising:
   a corona charger for ionizing the aerosol particles;
   a corona electrometer for measuring corona leakage current;
   a first condenser for ion trapping aerosol particles charged by the corona charger, wherein the first condenser is adapted to trap aerosol particles having a first mobility; and
   a second condenser connectable to the first condenser, wherein the second condenser is adapted to trap aerosol particles having a plurality of mobilities.

2. The portable apparatus as in claim 1 further comprising a first adjustable high voltage power supply for adjusting an electric field associated with the first condenser.

3. The portable apparatus as in claim 1 further comprising a second adjustable high voltage power supply for adjusting an electric field associated with the second condenser.

4. The portable apparatus as in claim 1 further comprising a third adjustable high voltage power supply for adjusting the corona charger ionizing power.

5. The portable apparatus as in claim 1 further comprising a first electrometer for measuring current associated with the particles trapped by the first condenser.

6. The portable apparatus as in claim 1 further comprising a second electrometer for measuring current associated with the particles trapped by the second condenser.

7. The portable apparatus as in claim 1 further comprising a measurement board for determining particle sizes and concentrations in the aerosol.

8. The portable apparatus as in claim 4 further comprising:
   a flow meter for measuring the aerosol flow through the portable apparatus; and
   a pump controller connectable to the flow meter, wherein the pump controller increases or decreases the aerosol flow through the portable apparatus.

9. The portable apparatus as in claim 8 further comprising: a control board for monitoring measurements by the measurement board, adjusting the pump controller, adjusting the first adjustable high voltage power supply, adjusting the second adjustable high voltage power supply, and adjusting the third adjustable high voltage power supply.

10. The portable apparatus as in claim 9, wherein the control board comprises:
    at least one mote for interaction with the control board;
    at least one GPS transceiver for determining global positioning location information associated with the portable apparatus; and
    at least one radio frequency identification tag (RFID) for identification information associated with the portable apparatus.

11. The portable apparatus as in claim 1, further comprising an aerosol inlet impactor.

12. A portable apparatus for measuring aerosol particle concentration and particle size distribution, the apparatus comprising:
    a corona charger for ionizing the aerosol particles;
    a corona electrometer for measuring corona leakage current;
    a first condenser for ion trapping aerosol particles charged by the corona charger, wherein the first condenser is adapted to trap aerosol particles having a first plurality of mobilities.

13. A portable apparatus as in claim 12 further comprising
    a second condenser connectable to the first condenser, wherein the second condenser is adapted to trap aerosol particles having a second plurality of mobilities; and
    a third condenser connectable to the first condenser, wherein the third condenser is adapted to trap aerosol particles having a third plurality of mobilities.

14. A portable apparatus as in claim 12 further comprising at least one dual condenser connectable to the first condenser, wherein the at least one dual condenser is adapted to trap aerosol particles having a fourth plurality of mobilities.

15. A portable apparatus as in claim 12, further comprising at least one condenser set connectable to the first condenser, wherein the at least one condenser set comprises at least one condenser, wherein the at least one condenser is adapted to trap aerosol particles, having a fifth plurality of mobilities.

16. A portable apparatus for measuring aerosol particle concentration and particle size distribution, the apparatus comprising:
    a corona charger for ionizing the aerosol particles;
    a corona electrometer for measuring corona leakage current;
    a first condenser for ion trapping aerosol particles charged by the corona charger, wherein the first condenser is adapted to trap aerosol particles having a first mobility;
    a second condenser connectable to the first condenser, wherein the second condenser is adapted to trap aerosol particles having a plurality of mobilities a pump controller for adjusting the aerosol flow rate through the apparatus; and a measurement board for determining particle sizes and concentrations in the aerosol.

17. The portable apparatus as in claim 16 further comprising:

a first adjustable high voltage power supply for adjusting an electric field associated with the first condenser;

a second adjustable high voltage power supply for adjusting an electric field associated with the second condenser, a third adjustable high voltage, power supply for adjusting the corona charger ionizing power;

a first electrometer for measuring current associated with the particles trapped by the first condenser; and a second electrometer for measuring current associated with the particles trapped by the second condenser.

18. The portable apparatus as in claim 16 further comprising: a control board for monitoring measurements by the measurement board, adjusting the pump controller, adjusting the first adjustable high voltage power supply, adjusting the second adjustable high voltage power supply, and adjusting the third adjustable high voltage power supply.

19. The portable apparatus as in claim 18, wherein the control board comprises:

at least one mote for interaction with the control board;

at least one GPS transceiver for determining global positioning location information associated with the portable apparatus; and at least one radio frequency identification tag (RFID) for identification information associated with the portable apparatus.

20. The portable apparatus as in claim 16, further comprising an aerosol inlet impactor.

* * * * *